United States Patent [19]
Senkan et al.

[11] 4,199,022
[45] Apr. 22, 1980

[54] METHOD OF FREEZING LIVING CELLS AND TISSUES WITH IMPROVED SUBSEQUENT SURVIVAL

[75] Inventors: Selim M. Senkan; Gerald P. Hirsch, both of Oak Ridge, Tenn.

[73] Assignee: The United States of America as represented by the Department of Energy, Washington, D.C.

[21] Appl. No.: 967,748

[22] Filed: Dec. 8, 1978

[51] Int. Cl.² ............................................. F25B 13/00
[52] U.S. Cl. ............................................. 165/2; 62/78; 435/2; 424/101
[58] Field of Search ................... 62/62, 64, 78; 165/2; 195/1.7, 1.8; 424/101

[56] References Cited
U.S. PATENT DOCUMENTS

| 4,030,314 | 6/1977 | Strehler et al. | 62/78 |
| 4,117,881 | 10/1978 | Williams et al. | 165/2 |

Primary Examiner—Ronald C. Capossela
Attorney, Agent, or Firm—R. V. Lupo; Stephen D. Hamel; Louis M. Deckelmann

[57] ABSTRACT

This invention relates to an improved method for freezing red blood cells, other living cells, or tissues with improved subsequent survival, wherein constant-volume freezing is utilized that results in significantly improved survival compared with constant-pressure freezing; optimization is attainable through the use of different vessel geometries, cooling baths and warming baths, and sample concentrations.

7 Claims, 4 Drawing Figures

METHOD OF FREEZING LIVING CELLS AND TISSUES WITH IMPROVED SUBSEQUENT SURVIVAL

BACKGROUND OF THE INVENTION

This invention was made in the course of, or under, a contract with the U.S. Department of Energy.

The ability to store living cells and tissues in the frozen state would be very valuable in medical applications such as organ banks. Red blood cells, spermatozoa, and other unicellular organisms have been successfully frozen at atmospheric pressure by using cryoprotective agents such as glycerol or dimethyl sulfoxide (DMSO), although the protective mechanism of these agents is not well understood. It has been postulated that freeze damage occurs because of the formation of intracellular ice during rapid freezing or because of cell dehydration and solute concentration during slow freezing, in which pure ice forms externally to the cell. Accordingly, the survival of red blood cells, other living cells, or tissues taken through a freezing-thawing sequence utilizing constant-pressure freezing is not as great as desired because of the above-mentioned freeze damage. Thus, there exists a need to provide an improved method for improving the survival of red blood cells, other living cells, or tissues taken through a freezing-thawing sequence. The present invention was conceived to meet this need in a manner to be described below.

SUMMARY OF THE INVENTION

It is the object of the present invention to provide an improved method for preserving red blood cells, other living cells, or tissues taken through a freezing-thawing sequence.

The above object has been accomplished in the present invention by freezing a sample of living cells or tissues in a vessel capable of withstanding rupture when completely filled, sealed, and the temperature lowered to $-196°$ C., to freeze the cells or tissues at constant volume; and increasing the temperature to above the freezing temperature of the sample to thaw the cells or tissues. It has been determined that constant-volume freezing significantly increased cell or tissue survival compared with constant-pressure freezing under similar conditions, and fast warming also increases the survival.

DESCRIPTION OF THE PREFERRED EMBODIMENT

The following description relates to the preserving of red blood cells taken through a freezing-thawing sequence and it should be understood that the present method is equally applicable to all living cells and tissues.

Figure 1:
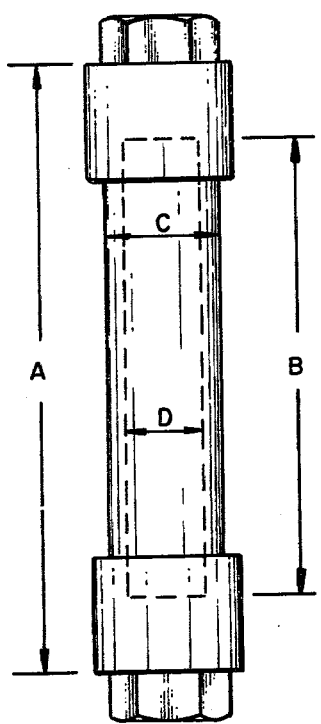
FIG. 1 is a sectional view of a stainless steel vessel utilized in the present method.

A typical, commercially available stainless steel vessel utilized for constant-volume freezing is illustrated in FIG. 1 of the drawings. Various vessel configurations that were utilized for testing the effects of cooling and warming rates on the survival rates are listed in the following Table I:

TABLE 1

| Vessel | $\dfrac{\text{Surface Area}}{\text{Volume}}$ cm$^{-1}$ | Dimensions (cm) | | | |
|---|---|---|---|---|---|
| | | A | B | C | D |
| I | 4.3 | 8.9 | 6.4 | 1.4 | 1.0 |
| II | 2.8 | 22.9 | 19.1 | 2.1 | 1.5 |
| III | 2.4 | 5.1 | 2.5 | 5.1 | 2.5 |

The blood samples utilized in the various tests, to be discussed hereinbelow, consisted of 1% fresh rabbit blood, 4% citrate glucose solution, and 95% 0.15-M NaCl aqueous solution (V/V). Dilute solutions were used to isolate cell-to-cell interactions. It should be noted that suspension in a diluting solution is not necessary but was employed only for testing purposes. After freezing, red cell survival was determined by centrifuging the blood samples and measuring the optical density of the supernatant, which is proportional to the percent hemolysis. A Beckman DB spectrophotometer using a wavelength setting of 540 nm was used to measure optical densities. The instrument was recalibrated for each batch of diluted blood by using a 100% hemolysis standard of the same composition.

The various vessels utilized in the tests were first cleaned and then rinsed with diluted blood. After being filled with respective samples and tightly sealed, they were immersed in the desired constant-temperature bath and allowed to come to thermal equilibrium. Various cooling and warming rates were achieved using liquid nitrogen ($-196°$ C.); a dry ice-acetone mixture ($-78°$ C.); 3-pentanone slush ($-40°$ C.); and warm water ($37°$ C.) as constant-temperature baths.

The cooling and subsequent warming were done in either one or two steps, with final thawing at $37°$ C. in accordance with the following Table 2:

TABLE 2

| | Immersion Time (min) for Cooling and Warming Processes | | | | | | | | | | | |
|---|---|---|---|---|---|---|---|---|---|---|---|---|
| | Vessel Type and Bath Temperature | | | | | | | | | | | |
| | I (°C.) | | | | II (°C.) | | | | III (°C.) | | | |
| Process | 37 | −40 | −78 | −196 | 37 | −40 | −78 | −196 | 37 | −40 | −78 | −196 |
| One-step cooling | — | 15 | 10 | 10 | — | 20 | 10 | 10 | — | 20 | 10 | 10 |
| Two-step cooling | — | 15 | 10 | 10 | — | 20 | 10 | 10 | — | — | — | — |
| One-step warming | 3 | — | — | — | 6 | — | — | — | 8 | — | — | — |
| Two-step warming | 3 | 15 | 10 | — | 6 | 15 | 10 | — | 8 | — | — | — |

The vessel types are shown in the above Table 1. The thawed samples were then removed from the vessels, centrifuged, and the percent hemolysis measured with the spectrophotometer.

Vessel geometry and bath temperatures affect the rate of cooling as shown in the following Table 3, and thus influence survival rates.

TABLE 3

| | Cooling Rates (° C./min) | | |
| --- | --- | --- | --- |
| | Cooling Baths | | |
| | −40° C. | −78° C. | −196° C. |
| Vessel I | 90 | 230 | 250 |
| Vessel II | 20 | 80 | 120 |

Figure 2:
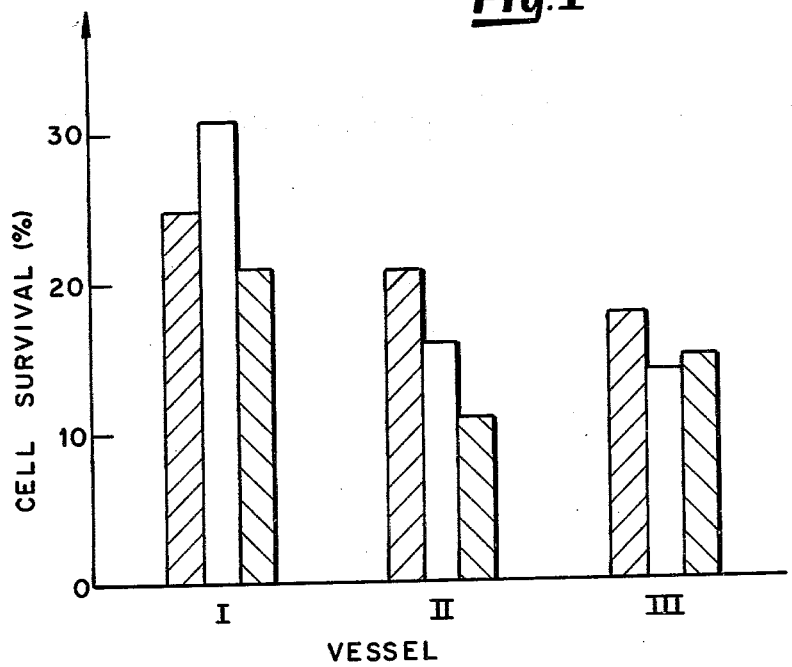
FIG. 2 is a graph illustrating the effect of vessel geometry on cell survival.

Since the ratio of surface area to sample volume influences the heat transfer rate to the amount of sample to be frozen, it relates the effect of vessel geometry to cell survival. As seen in FIG. 2, which presents the data of the following Table 4, vessels I, II, and III with surface-area-to-volume ratios (cm$^{-1}$) of 4.3, 2.8, and 2.4, respectively, affect survival. The relationship is particularly clear for the −40° C. and −78° C. baths.

TABLE 4

| Cell Survival in One-Step Cooling and Warming Processes | | | |
| --- | --- | --- | --- |
| | Cooling Baths | | |
| | −40° C. | −78° C. | −196° C. |
| Vessel I | 25% | 31% | 21% |
| Vessel II | 21% | 16% | 11% |
| Vessel III | 18% | 14% | 15% |

For a given vessel geometry, the data of Table 3 indicate that a higher bath temperature decreases the cooling rate. Thus, it can be seen from FIG. 3 that lower cooling rates seem to increase cell survival.

Figure 3:
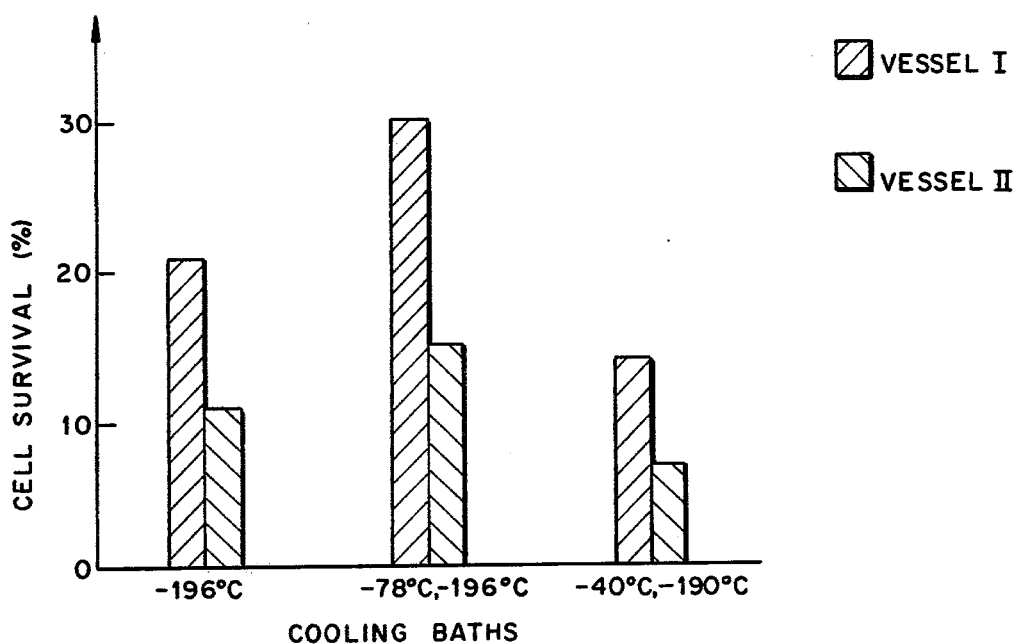
FIG. 3 is a graph illustrating the effect of cooling rate on cell survival.

Since the data in FIG. 3 reflect the effects of final temperatures as well as cooling rate, two-step cooling experiments in which all samples reach the same final temperature (−196° C.) were conducted and the results are shown in the following Table 5.

TABLE 5

| Cell-Survival in Two-Step Cooling, One-Step Warming Processes | |
| --- | --- |
| | Cooling Baths |
| | −40° C., −196° C. | −78° C., −196° C. |
| Vessel I | 14% | 30% |
| Vessel II | 7% | 15% |

Besides isolating the effects of initial cooling rates, these experiments show the possibilities of cooling samples down to a low temperature suitable for long-term storage. The results, shown in FIG. 3, indicate that for both vessels I and II initial cooling in the −78° C. bath gave the best survival rates.

From the above Tables 4 and 5, it can be seen that cell survival is essentially the same for one- and two-step cooling processes using the −78° C. bath, meaning that little or no cell damage occurs when cooling below −78° C. A similar comparison with the −40° C. bath shows that far fewer cells survived the two-step process, indicating that the initial slow freezing may dehydrate the blood cells and somehow leave them susceptible to damage during further cooling.

Figure 4:
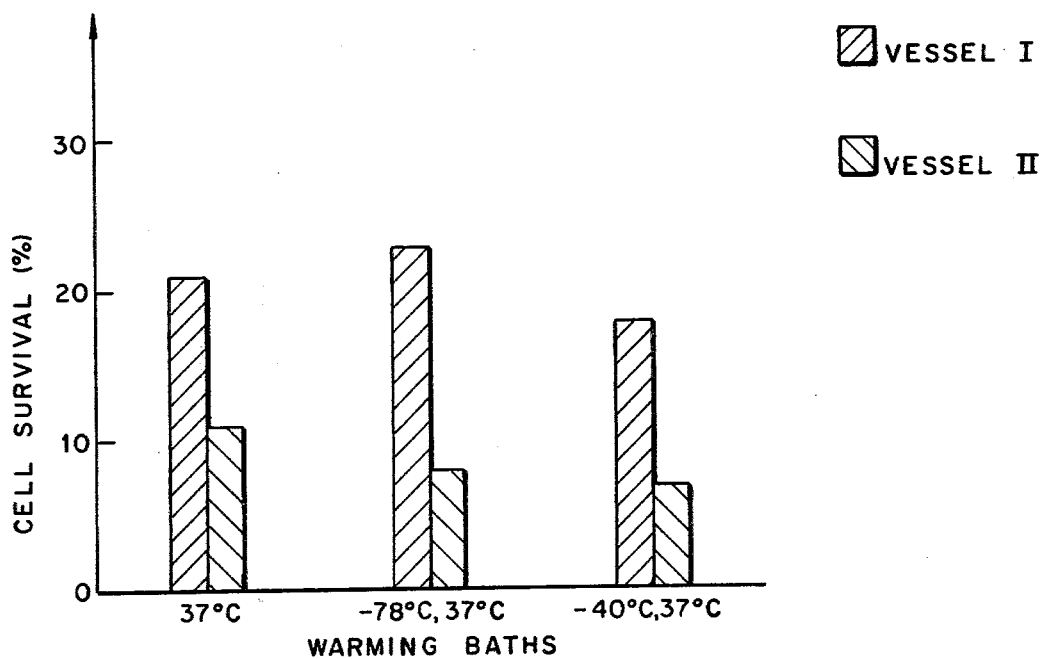
FIG. 4 is a graph illustrating the effect of warming rate on cell survival.

Two-step warming processes in which all samples were initially frozen in the −196° C. bath were conducted to see if slower warming affected cell survival and the results are shown in FIG. 4 and in the following Table 6:

TABLE 6

| Cell Survival in One-Step Cooling, Two-Step Warming Processes | | |
| --- | --- | --- |
| | Warming Baths from −196° C. | |
| | −40° C., 37° C. | −78° C., 37° C. |
| Vessel I | 18% | 23% |
| Vessel II | 7% | 8% |

In FIG. 4, it can be seen that warming initially in the −40° C. bath gave slightly lower survivals than did the other processes. Attempts to thaw samples in ice water (0° C.) and room temperature air (25° C.) produced almost no cell survival. Thus, it appears that relatively rapid and direct thawing is best since cell damage due to ice recrystallization is avoided.

Experiments using two-step cooling and warming processes were conducted and the results are shown in the following Table 7.

TABLE 7

| Cell Survival in Two-Step Cooling, Two-Step Warming Processes | |
| --- | --- |
| Constant Temperature Baths | |
| −40° C., −196° C., | −78° C., −196° C. |
| −40° C. | −78° C. |
| Vessel I 10% | 19% |
| Vessel II 5% | 13% |

It can be seen from Table 7 that the best intermediate bath temperature for either vessel I or II was −78° C., in agreement with results of previous two-step processes.

Cell survival rates for constant-volume and constant-pressure freezing are shown in the following Table 8:

TABLE 8

| Cell Survival in Constant-Volume and Constant-Pressure Freezing | |
| --- | --- |
| Cooling Bath = −40° C. | Warming Bath = −37° C. |
| Constant Volume | Constant Pressure |
| Vessel I 25% | 13% |
| Vessel II 21% | 6% |

It should be noted that cell survival during constant-pressure freezing was determined by cooling vessels that had been only 80% filled with diluted blood.

It can be seen from Table 8 that constant-volume freezing significantly increased red blood cell survival compared with constant-pressure freezing under similar conditions. This cryoprotective effect may be due to the elimination of ice expansion, which prevents damage to cell membranes.

Also, from Tables 4 and 5, it can be seen that cell survival also is improved in vessels with high surface-area-to-volume ratios, and that initial freezing in the −78° C. bath gave the best survival rates as mentioned hereinabove. In addition, a fast warming in the 37° C. bath increases cell survival compared with slower warming rates.

This invention has been described by way of illustrated rather than by limitation and it should be apparent that it is equally applicable in fields other than those described.

What is claimed is:

1. A method for increasing survival of living cells taken through a freezing-thawing sequence comprising the steps of placing a sample of said cells in a freezing vessel capable of withstanding rupture when completely filled and sealed; rapidly cooling said filled, sealed vessel to a temperature of about −78° C. at constant volume; and rapidly heating said vessel to a temperature of about 37° C. to thaw said cells, whereby the constant-volume freezing and thawing substantially increase the cell survival compared with conventional constant-pressure freezing and thawing.

2. The method set forth in claim 1, and including between said cooling step and said heating step the further steps of sequentially cooling said vessel to a lower temperature of about −196° C. at constant volume, and heating said vessel to a temperature of about −78° C.

3. The method set forth in claim 1, wherein said sample is red blood cells.

4. The method set forth in claim 2, wherein said sample is red blood cells.

5. The method set forth in claim 1, wherein said sample is a diluted blood cell suspension consisting of 1% fresh blood, 4% citrate glucose solution, and 95% 0.15-M NaCl aqueous solution (V/V).

6. The method set forth in claim 1, wherein said vessel has a surface-area-to-volume ratio of 4.3 cm$^{-1}$.

7. The method set forth in claim 2, wherein said vessel has a surface-area-to-volume ratio of 4.3 cm$^{-1}$.

* * * * *